(12) United States Patent
Teague

(10) Patent No.: US 8,405,502 B2
(45) Date of Patent: Mar. 26, 2013

(54) IDENTIFICATION AND CONNECTIVITY GATEWAY WRISTBAND FOR HOSPITAL AND MEDICAL APPLICATIONS

(75) Inventor: Edward Harrison Teague, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 855 days.

(21) Appl. No.: 12/482,175

(22) Filed: Jun. 10, 2009

(65) Prior Publication Data

US 2010/0315225 A1  Dec. 16, 2010

(51) Int. Cl.
*G08B 1/08* (2006.01)
*G08B 23/00* (2006.01)
*G08B 13/14* (2006.01)
*G08B 5/22* (2006.01)

(52) U.S. Cl. ............. 340/539.12; 340/539.1; 340/572.1; 340/573.1; 340/286.02; 340/286.07

(58) Field of Classification Search .................. None
See application file for complete search history.

(56) References Cited

U.S. PATENT DOCUMENTS

| 5,931,764 | A  | * | 8/1999  | Freeman et al.    | 482/4     |
|-----------|----|---|---------|-------------------|-----------|
| 6,954,148 | B2 | * | 10/2005 | Pulkkinen et al.  | 340/572.1 |
| 8,040,246 | B2 | * | 10/2011 | Graves et al.     | 340/573.1 |
| 2006/0066449 | A1 | * | 3/2006  | Johnson        | 340/539.12 |
| 2006/0238333 | A1 | * | 10/2006 | Welch et al.   | 340/539.12 |
| 2009/0030967 | A1 |   | 1/2009  | Loda           |            |
| 2009/0149722 | A1 | * | 6/2009  | Abolfathi et al. | 600/301  |
| 2009/0322513 | A1 | * | 12/2009 | Hwang et al.   | 340/539.12 |

FOREIGN PATENT DOCUMENTS

| WO | WO2006102537 A2 | 9/2006 |
| WO | WO2008014432 A2 | 1/2008 |

OTHER PUBLICATIONS

International Search Report and Written Opinion—PCT/US2010/038198, International Search Authority—European Patent Office—Nov. 30, 2010.

* cited by examiner

*Primary Examiner* — Julie Lieu
(74) *Attorney, Agent, or Firm* — James T. Hagler

(57) ABSTRACT

A communication gateway wristband serves as a source of patient identification and as an interface between a personal area network (PAN) of miniaturized electronic medical sensors on a patient and a wireless wide-area network (WWAN) such as a hospital network. The gateway wristband includes a PAN transceiver which can establish wireless data links with wireless medical sensors, a WWAN transceiver which can establish a wireless data link with WWAN infrastructure, a memory which stores a patient identifier, and a processor which receives data via the PAN transceiver and relays the patient identifier and the received data to an external network via the WWAN transceiver. The processor manages communications with both the PAN and WWAN transceivers, stores received sensor data in memory, and translates data from the PAN protocol to the WWAN protocol so that sensor data is relayed to the hospital infrastructure.

12 Claims, 14 Drawing Sheets

IDENTIFICATION AND CONNECTIVITY GATEWAY WRISTBAND FOR HOSPITAL AND MEDICAL APPLICATIONS

FIELD OF THE INVENTION

The present invention relates generally to computer network communications, and more specifically to methods and devices for identifying patients and relaying medical sensor data to hospital computer networks.

BACKGROUND

Medical facilities like hospitals face many challenges, including accurately tracking patients and the medications administered to them. Typically, patients are provided with a plastic wristband when they are admitted to a medical facility which includes their identifying information, such as name and a hospital record identifier. Procedures for tracking patients and administering medications involve numerous checks of each patient's wristband by nurses and doctors throughout the day. While generally effective, this manual inspection of wristbands can be inefficient and is prone to human error.

Another challenge facing hospitals involves the integration of new medical sensor technology and the associated volume of medical sensor data with patients' medical records and the hospital's information system infrastructure. With the continued miniaturization of electronic components it is anticipated that the medical industry will deploy ever smaller electronic medical sensors which can be placed on or within a patient to record and report any of variety of medically important parameters. Current methods for connecting medical sensors to patients use wires and cables stretching between the sensor on the patient and a monitoring system positioned nearby. As a result, a typical critical care patient may be attached to dozens of wires and tubes leading to medical monitoring systems. The resulting tangle of leads and tubes can interfere with the care provided to patients and lead to potential hazards.

SUMMARY

The various embodiments provide convenient solutions for identifying patients and linking miniaturized electronic medical sensors to a hospital information system infrastructure. A patient identifier wristband contains a wireless communication gateway device, which is referred to herein as a "gateway wristband." The gateway wristband is configured to store and wirelessly report a patient identifier (ID) to the hospital information system infrastructure, such as a network server. The patient ID may be an identifier that is specifically assigned to the patient or may be an identifier assigned to the gateway wristband ("wristband ID") that can be linked to the patient in a data file stored in the hospital information system infrastructure, such as a patient record database.

The gateway wristband may serve as a wireless gateway for a wireless personal area network (PAN) of miniaturized electronic medical sensors applied to the patient via a first transceiver ("PAN transceiver"). The gateway wristband may also serves as a communication node on a wireless local-area network (WLAN) or wireless wide-area network (WWAN) such as the hospital wireless network via a second transceiver (WLAN or WWAN transceiver). The gateway wristband may also include a memory for storing the patient or device ID, and a processor which controls the PAN and WLAN transceivers. The processor may be configured with software instructions to receive data via the PAN transceiver and relay received data along with the patient or wristband ID to an external network via the WLAN transceiver. The processor may be further configured to manage communications with both the personal area network and the wireless wide-area network, store received sensor data when necessary, and translate received data from the PAN protocol format to the WLAN or WWAN protocol format so that data can be reliably relayed from the sensors to the hospital's information system infrastructure. The processor may further be configured to implement communication security measures in communications with both the personal area and local-area networks as may be necessary to protect patient data and ensure system reliability. The gateway wristband may also include an internal power source with the electronics sealed within a waterproof housing so that it is compatible with the hospital environment. In an embodiment, the gateway wristband may also or alternatively include a cellular telephone transceiver configured to establish a cellular data communication link so that the gateway wristband can relay received data to a hospital network via a cellular telephone network.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
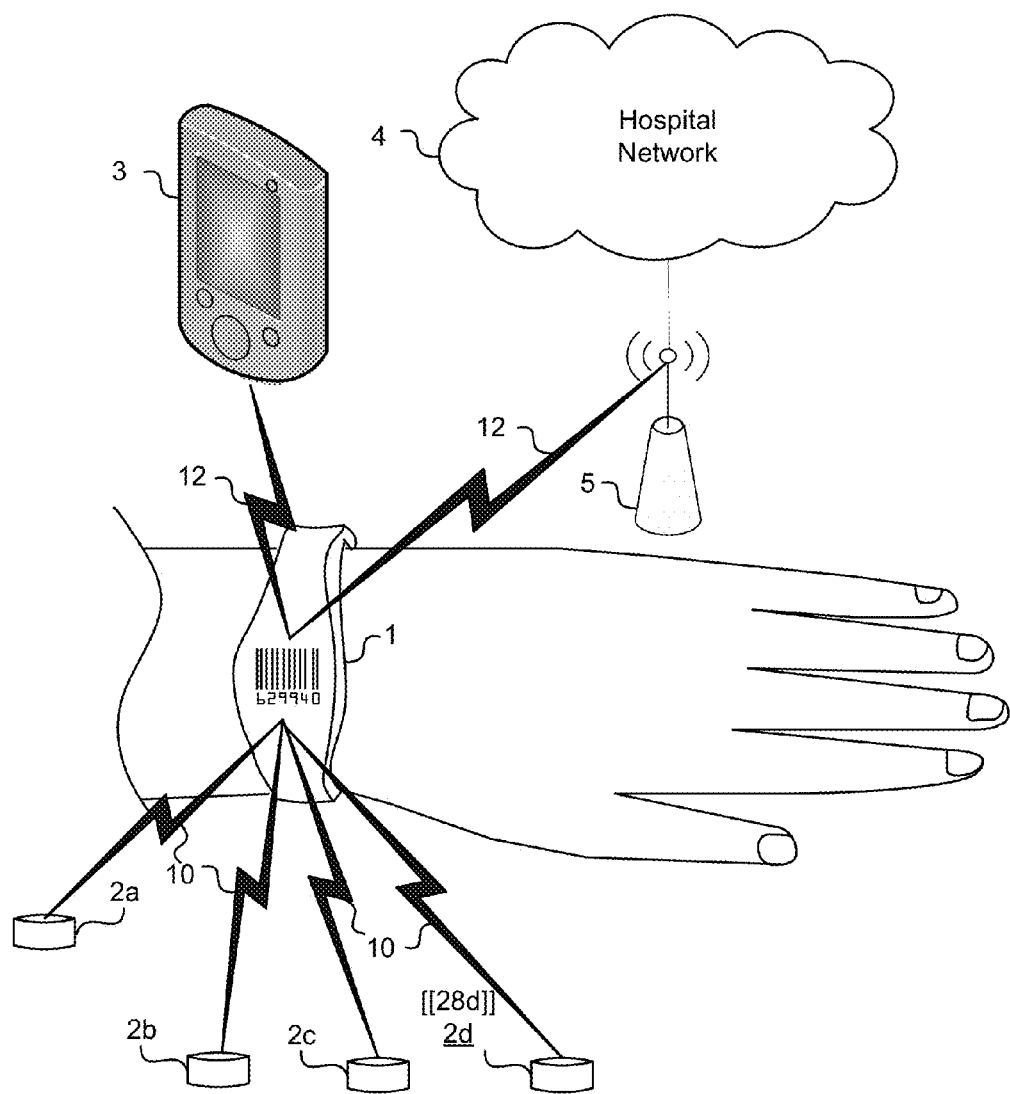
FIG. 1 is a communication system block diagram of a communication network which includes a gateway wristband linking medical sensors on a patient to a hospital wireless communication network according to an embodiment.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

As used herein, the terms "mobile computing device" and "handheld device" refer to any one or all of cellular telephones, personal data assistants (PDA's), palm-top computers, wireless electronic mail receivers and cellular telephone receivers (e.g., the Blackberry® and Treo® devices), multimedia Internet enabled cellular telephones (e.g., the Blackberry Storm®), and similar personal electronic devices which include a programmable processor and memory, a wireless communication transceiver.

Tracking patients and ensuring that correct medications are administered to them remains a persistent challenge in the medical industry. The most common method for identifying patients involves labeling them with a patient identification (ID) wristband when they are admitted. Typical patient ID wristbands are plastic strips printed with patient identifying information (e.g., name and/or ID number). Some patient ID wristbands include a barcode which can be read using a conventional barcode reader. The most common approach for ensuring patients receive proper medications involves comparing the patient ID information on the wristband with patient ID information associated with the medication. In automated facilities, a barcode reader may be used to read the barcode on the patient ID wristband and on barcodes attached to medicines or food trays. Such manual checking of patient IDs may be repeated several times a day as part of hospital procedures to reduce the chance of medical mistakes.

With the continued miniaturization of electronic components it is anticipated that the medical industry will soon deploy miniaturized electronic medical sensors which can be placed on or within a patient to record and report any of variety of medically important parameters. In order to reduce the clutter and confusion in the hospital environment, such miniaturized electronic medical sensors may be made wireless thereby obviating the need for wires connecting them to a data collection unit. To keep the size and power requirements of miniaturized electronic medical sensors to a minimum, such sensor devices are likely to use low-power wireless data links. A number of low power wireless data link protocols are available which are suitable for such purposes. Due to the limited range of such low-power wireless transceivers such communication links are often referred to as "personal area networks" (PAN), which is the term used herein to refer to networks which encompass a particular patient. A PAN transceiver typically has the range of a few feet and thus encompasses the area around a person but does not extend much further, and thus does not interfere or interact with other wireless networks. While such short range communication protocols provide convenient and energy-efficient communication links, such protocols are generally incompatible with wireless wide-area networks due to their limited range as well as incompatible waveforms and information encoding schemes.

Wireless local-area networks (WLAN) are widely deployed as part of the network infrastructure of institutions, such as hospitals, due to their ease of use and high data transmission rates. Examples of wireless local-area communication network protocols including IEEE 802.11 (WiFi), and WiMax. Institutions may also employ wireless wide-area networks (WWAN) which may use communication technologies providing wide area coverage, such as cellular networks like CDMA2000 and UMTS.

The incompatibilities between the WLAN or WWAN infrastructure of most hospital facilities and personal area networks that are likely to be used with miniaturized electronic medical sensors could limit the adoption of new medical technologies unless a solution to this problem is provided. In order for miniaturized electronic medical sensors to be effectively deployed in a hospital environment, a communication interface or gateway must be provided to relay sensor data from sensor networks to the institution's wireless wide-area network infrastructure.

The various embodiments resolve both problems of identifying patients and linking miniaturized electronic medical sensors to hospital wireless wide area networks with a wristband wireless communication gateway device ("gateway wristband"). The gateway wristband serves as a wireless gateway for both the personal area network (PAN) comprising miniaturized electronic medical sensors on or within a particular patient and a wireless local-area network (WLAN) such as a hospital's wireless network. Such a gateway wristband includes a PAN communication transceiver which can establish a wireless data link with short range (i.e., PAN protocol) transceivers, a WLAN communication transceiver which can establish a wireless data link with local and wide-area wireless transceivers, a memory which stores a unique identifier for the patient or the wristband, and a processor which can receive data via the PAN transceiver and relay the received data and the patient or wristband ID to an external network via the WLAN transceiver. The processor is configured with software instructions to manage communications with both the personal area network and the wireless wide-area network, store received sensor data when necessary, and translate data from the PAN protocol format to the WLAN protocol format so that data can be reliably relayed from the sensors to the hospital infrastructure. The processor may further be configured to implement communication security measures in communications with both the personal area and wide-area networks as may be necessary to protect patient data and ensure system reliability. The gateway wristband may also include an internal power source and be sealed within a waterproof housing so that it is compatible with the hospital environment.

The PAN transceiver is not necessarily limited to any particular protocol, and instead may encompass any relatively short range or limited area wireless communication link. Using proximity-limited communication links help to simplify the system architecture by reducing the potential that the gateway wristband will detect and try to establish communication links with miniaturized electronic medical sensors on another patient. Examples of PAN protocols which may be used in the various embodiments include Bluetooth®, IEEE 802.15.4, and Zigbee® wireless communication protocols and standards. In addition to these PAN protocols, wireless proximity-limited communication links may be established using other close range communication media, including for example radiofrequency identification (RFID) tag and the IrDA (Infrared Data Association) protocols. Also, other close range wireless protocols and standards may be developed and may be used in the various embodiments in the same manner as described herein. Further, longer range wireless communication protocols may be used with modifications or additions to limit their effective range to the vicinity of the patient's gateway wristband. For example, WiFi and WiMax wireless communication protocols could also be used in combination with range-limiting features. For example, the power of the miniaturized electronic medical sensor transmitters may be limited. As another example, round-trip communication delay limits may be imposed such that the sensor-gateway wristband communication links can only be established if the round trip of such signals is less than a threshold set to reject signals sent from more than a dozen feet or so, which may be as short as two to three feet separation.

The various embodiments may implement known fundamental communication security mechanisms such as device-to-device pairing, encrypted data links, integrity checking, and establishing a trust domain. As used herein, the term "trust domain" refers to a set of devices in possession of common or related credentials such that the devices can "trust" each other to share confidential information and exchange communications in a secure manner. An example of a trust domain is a pair (or more) of devices sharing a set of X0.509 certificates signed by a Certificate Authority, e.g., a PKI. Another example of a trust domain is a pair (or more) of devices sharing symmetric credentials. To extend a trust domain to another device, the receiving device needs to be verified as a valid new member, and the credentials need to be exchanged securely. Methods and devices for establishing trust domains among wireless communication nodes suitable for use with the various embodiments are disclosed in U.S. patent application Ser. No. 12/035,309 entitled "Method and Apparatus To Deploy Dynamic Credential Infrastructure Based on Proximity" filed Feb. 21, 2008, the entire contents of which are hereby incorporated by reference.

In a further embodiment, the gateway wristband may also include a close range communication (e.g., near field communication) transceiver for exchanging information useful for establishing secure communication links, such as exchanging network set up information, security credentials and encryption keys. References herein to "close range communication links" (CRCL) and "near field communications" (NFC) refer to links with a communication range limited to less than about one foot, and in some embodiments to approximately 0-20 cm (up to 8 in.). Methods and devices for using CRCL communication links to exchange tokens and other information for establishing trust domains among wireless communication nodes are disclosed in U.S. patent application Ser. No. 12/035,309 which is incorporated by reference above.

Typical PAN protocols provide for automatic exchanging of link establishment information. Thus, in an embodiment the gateway wristband may automatically detect and establish data communication links with miniaturized electronic medical sensors within range. For example, the gateway wristband and a miniaturized electronic medical sensor may exchange address and device identifier information (e.g., sensor ID or MAC ID) necessary to enable establishing a BlueTooth® wireless data link with no further synchronization activity or user action. As another example, the two devices may exchange Internet Protocol (IP) or local area network address information to enable communications with WiFi wireless or Ethernet-based networks.

FIG. 1 shows typical elements of a communication system including a gateway wristband 1 on a patient's wrist. The Gateway wristband 1 includes an internal PAN transceiver for establishing communication links 10 with a plurality of miniaturized electronic medical sensors 2a-2d, and a WLAN transceiver for establishing wide-area wireless communications links 12 with a base station 5 of a hospital network 4. The gateway wristband 1 may also establish communication links 12 with mobile computing devices such as a PDA 3 which may be carried by a physician or nurse. As described more fully below with reference to FIG. 11, the gateway wristband 1 includes one or more processors and memory which enable the device to receive sensor data from the miniaturized electronic medical sensors 2a-2d in a first communication protocol, such as PAN communication links 10, temporarily store the data if necessary, and relay the data to an external network in a second communication protocol, such as WLAN communication links 12 to a hospital network 4. Thus, the gateway wristband 1 serves as a communication interface gateway receiving data from a first network (e.g., a PAN network of miniaturized electronic medical sensors 2a-2d) in a first protocol and relaying it to a second network (e.g., the hospital network 4) in a second protocol.

In addition to acting as a communication gateway, the processor within the gateway wristband 1 is configured with software instructions to communicate a patient ID or a wristband ID (which is linked to the patient in a data table maintained within the hospital information system) to the hospital network 4 and/or to mobile computing devices 3, such as a nurse's PDA. The patient or wristband ID may be communicated to the hospital network 4 periodically so as to indicate the location of the patient within the network, as may be indicated by the particular base station 5 in communication with the gateway wristband 1. The patient or wristband ID may be communicated to a mobile computing device 3, such as a PDA, when the devices come in close proximity or when an operator (e.g., a nurse or doctor) presses a key to identify the patient. In this manner the gateway wristband 1 can help ensure that medications are given to patients accurately. Also, the patient or wristband ID may be communicated as part of the communication of sensor data so that the hospital network 4 can accurately correlate the received medical sensor data with the particular patient to whom it corresponds. As a further patient identification aid, the gateway wristband 1 may be imprinted with the patient's name, an ID number, and/or barcode which may be read in the same manner that conventional patient wristbands are reviewed today.

By providing a communication interface gateway, the gateway wristband 1 facilitates the use of miniaturized electronic medical sensors 2a-2d on patients by receiving data from the low-power sensor devices and relaying the data to the hospital network at a higher power and in a data format consistent with the hospital's WLAN system. As such, the gateway wristband 1 eliminates many of the wires and cumbersome devices that would otherwise be required to couple a patient's miniaturized electronic medical sensors 2a-2d to recording devices or the hospital network 4.

Figure 2:
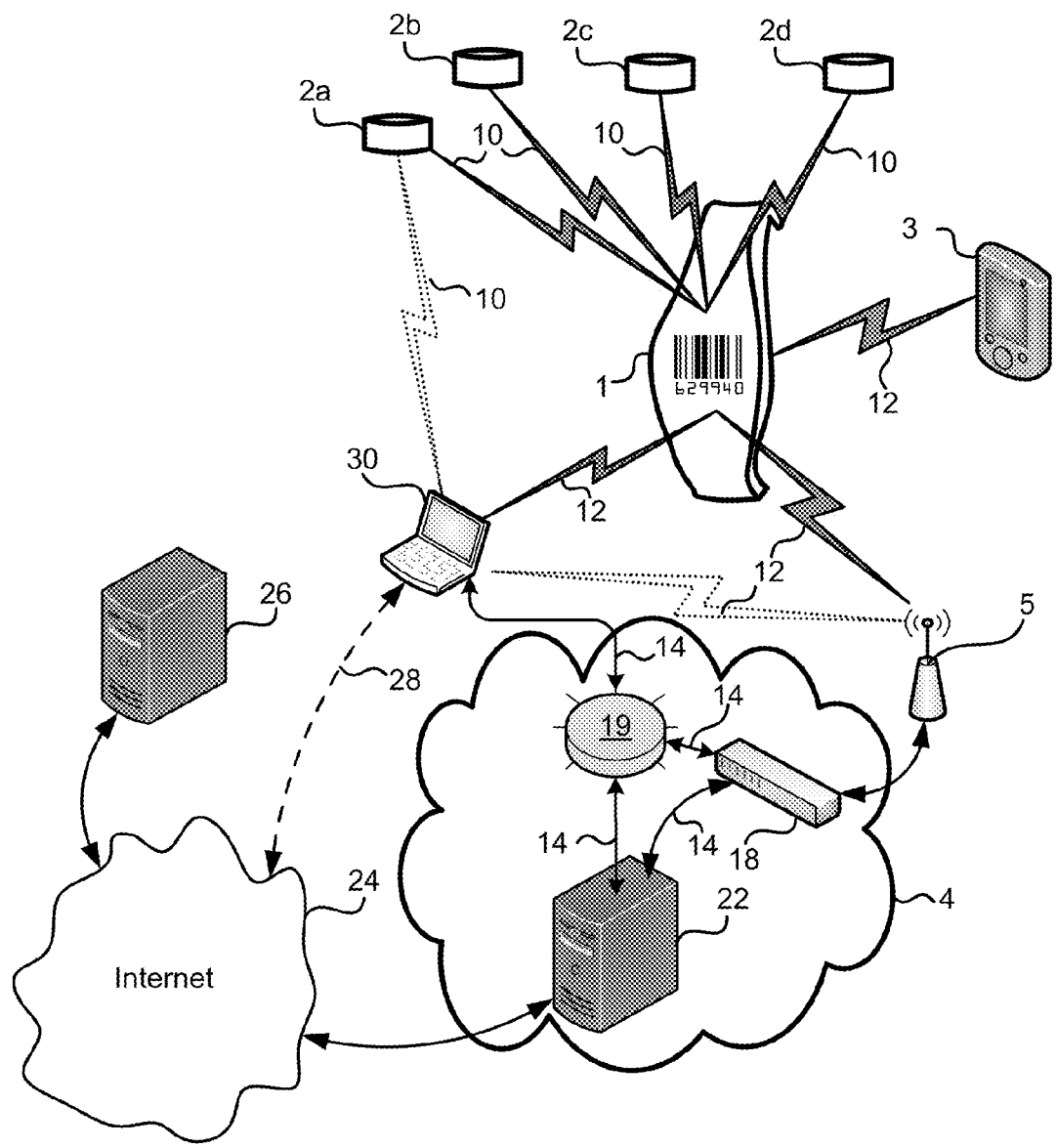
FIG. 2 is a communication system block diagram of a communication network which includes a gateway wristband linking medical sensors to a hospital communication network and the Internet according to an embodiment.

The communication links provided by the gateway wristband 1 may also enable connecting the patient and the patient's miniaturized electronic medical sensors to a wider area network, such as the Internet 24 as illustrated in FIG. 2.

This communication network includes a gateway wristband 1 including a WLAN or WWAN transceiver for transmitting and receiving data network signals over communication links 12 from/to a WLAN or WWAN base station 5. In this example network the base station 5 is coupled to the hospital network 4 which includes elements required to operate a wireless network, such as a plurality of wireless routers 18, coupled to elements required to operate a wired network, such as a router 19 and a network server 22, all of which may be couple by wired connections 14. Other computers 30 and monitors may be coupled to the hospital network 4 via wired connections 14 or wireless communication links 12 via the base station 5.

As is typical today, the hospital network 4 may be coupled to an external network such as the Internet 24. In a typical embodiment, a hospital network server 22 is coupled to the Internet 24 via an internet connection (not shown). In turn, other computers, such a laptop computer 30, can be coupled to the hospital network 4 via the Internet 24 by way of their own Internet connection 28. In a further embodiment, one or more servers 26 may be coupled to the Internet 24 and configured to receive data relayed by the gateway wristband 1, such as to be stored within a patient's electronic medial records maintained on the one or more servers 26.

As described above, the gateway wristband 1 includes a PAN transceiver that is configured to establish wireless personal area network connections with one or more miniaturized electronic medial sensors 2a-2d via PAN communication links 10. The gateway wristband 1 is configured to receive data from the miniaturized electronic medial sensors 2a-2d via the PAN communication links 10 and relay the data to the hospital network 4 via WLAN or WWAN communication links 12. Additionally, some mobile computing devices, such as a laptop computer 30, may also be configured with both a PAN transceiver, to receive data from miniaturized electronic medical sensors 2a-2d, and with a WLAN or WWAN transceiver to establish network communication links 12 with the hospital network 4 via a base station 5.

Figure 3A:
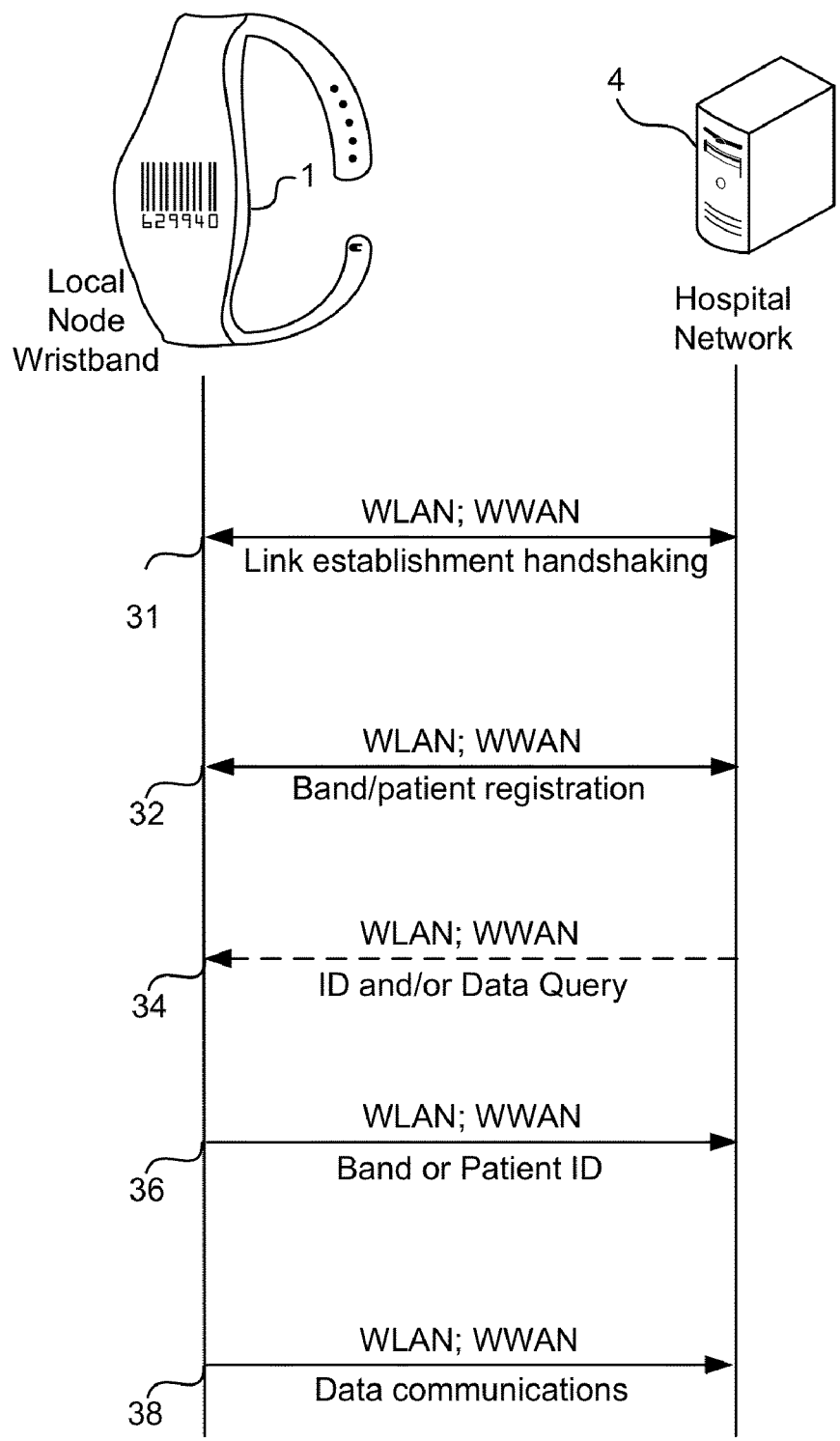
FIG. 3A is a message flow diagram of communications between a gateway wristband and a hospital network according to an embodiment.

The gateway wristband 1 may be configured to automatically establish wireless communications with a hospital network 4 or mobile computing device 3, such as a PDA. An example of messages that may be exchanged between a gateway wristband 1 and a hospital network 4 are illustrated in FIG. 3A. When the gateway wristband 1 senses a wireless wide-area network it may initiate link establishment handshaking messages 31 with that network. Such handshaking messages are determined by the particular communication protocol implemented by the WLAN or WWAN network and may be transmitted over the same WLAN or WWAN communication link as subsequent data communications. Once a communication link has been established, the gateway wristband 1 and the hospital network 4 may exchange registration messages 32 as necessary to correlate the gateway wristband 1 with the patient and the patient with the hospital network 4. For example, when a gateway wristband 1 is first placed on the wrist of the patient as part of a patient admission procedure, the gateway wristband 1 and hospital network 4 may exchange the registration messages 32 to enable the hospital network 4 to record the patient ID or wristband ID within a patient registry database. Once the patient registration process has been completed, subsequent communications may only transmit the patient ID or wristband ID to enable the hospital network 4 to identify the patient and correlate received sensor data with that particular patient. Once the network communication links are established and the patient and/or wristband have been registered with hospital network 4, the hospital network may periodically request the patient ID or patient data, optional data query message 34. Such a message may be addressed to the gateway wristband 1 and include a command instruction that the processor within the gateway wristband 1 can properly interpret. In response to receiving a patient ID or data query message 34 from the hospital network 4, the gateway wristband 1 may transmit the patient ID or wristband ID to the hospital network 4, message 36. The gateway wristband 1 then may began transmitting sensor data to the hospital network 4, messages 38.

Figure 3B:
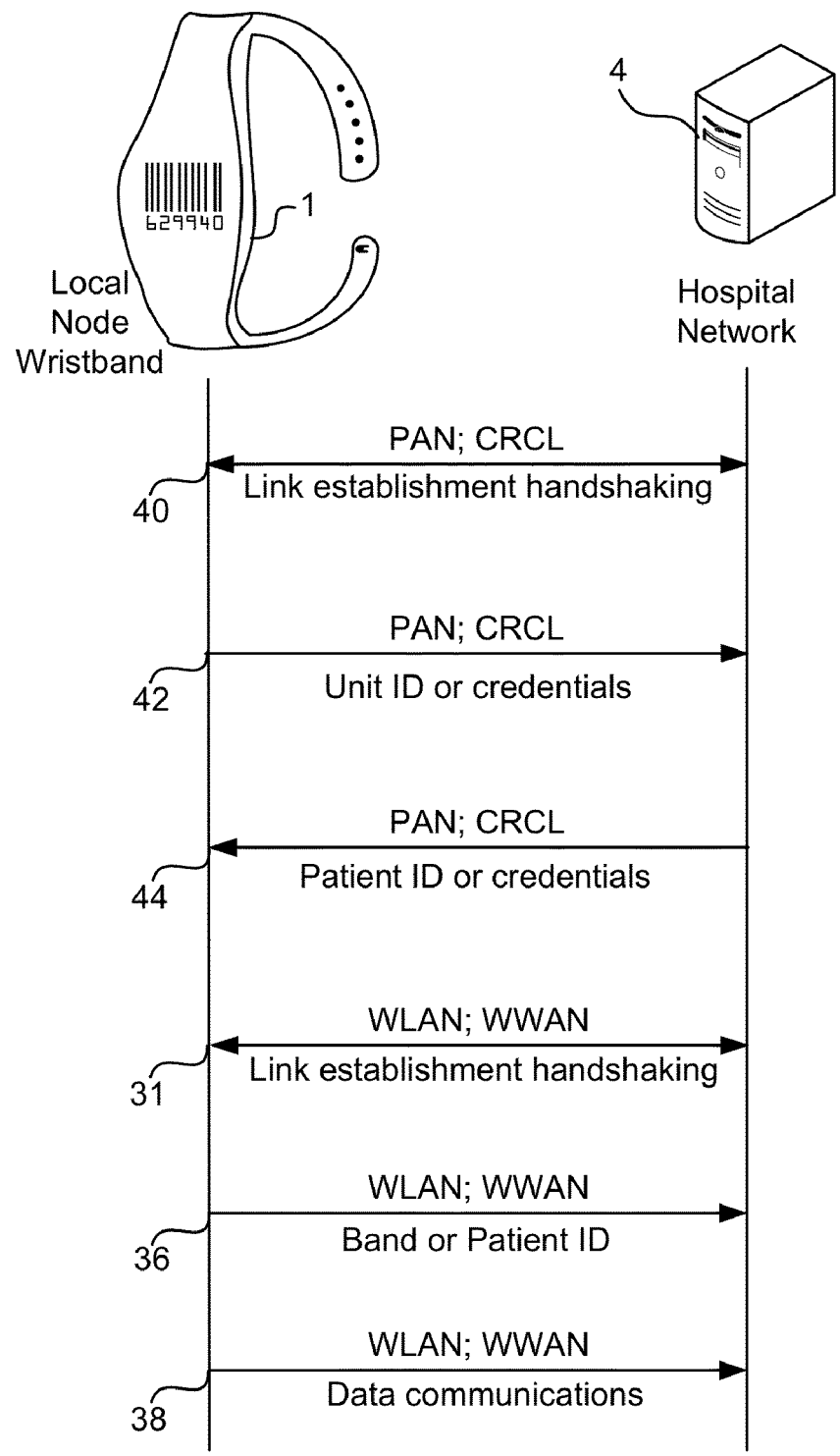
FIG. 3B is a message flow diagram of communications between a gateway wristband and a hospital network according to another embodiment.

In an embodiment, the gateway wristband 1 may include a CRCL transceiver configured to establish a CRCL communication link with a terminal on the hospital network 4 for purposes of conducting the registration procedure. Messages exchanged in this embodiment are illustrated in FIG. 3B. In this embodiment the process of registering the gateway wristband 1 with the hospital network 4 involves bringing the wristband into close proximity with a CRCL transceiver on the terminal within the hospital network 4. As soon as the gateway wristband 1 is within communication range of the CRCL transceiver on the hospital network 4 link establishment handshaking messages 40 will begin in order to establish a CRCL communication link. Once the CRCL communication link has been established, the gateway wristband 1 may transmit information identifying it to the hospital network 4 such as a wristband ID or similar credential message 42. The hospital network 4 may use the wristband ID or credentials to verify that the gateway wristband 1 is an authorized device, and if so the hospital network 4 may transmit patient ID or other credentials associated with the patient to the gateway wristband 1 for storage in memory, message 44. Since the patient ID and other patient information are necessarily private information, transmitting this information over a CRCL communication link provides inherent security due to its very short range. The gateway wristband 1 may save the patient ID or other information in memory for use in communicating the patient ID to the hospital network 4 or mobile computing devices 3. Once the registration information messages have been exchanged over the CRCL network, the gateway wristband 1 may be placed on the patient and moved outside the communication range of the hospital network CRCL terminal, thus ending the CRCL communication link. At this point, the gateway wristband 1 may automatically establish a WLAN or WWAN communication link with the hospital network 4 by exchanging link establishment handshaking messages 31 as described above with reference to FIG. 3A. Once the wireless communication link is established with the hospital network 4, the gateway wristband 1 may transmit the patient ID, message 36, and sensor data, message 38, as described above with reference to FIG. 3A.

The registration process described above need not be limited to a CRCL communication link, and instead may be accomplished using a personal area network (PAN) (i.e., an intermediate range network communication link) as noted in FIG. 3B. In this embodiment, the hospital network 4 may include a terminal configured with a PAN transceiver. When the gateway wristband 1 is brought within range of that network PAN transceiver, the link establishment handshaking messages 40 may be exchanged. Once that PAN communication link is established, the wristband ID or credentials may be transmitted to the hospital network 4 over the PAN communication link. Similarly, the hospital network 4 may transmit patient ID or other information to the gateway wristband 1 via that same PAN communications link, message 44. In order to avoid inadvertently establishing PAN communication links between the gateway wristband 1 and the hospital network 4, such a PAN transceiver may be limited to one or a few terminals that are removed from the patient treatment areas. For example, hospital network PAN transceivers may be included in terminals located only in areas where patients are admitted to the hospital (i.e., where gateway wristbands 1 are attached to patients).

Figure 3C:
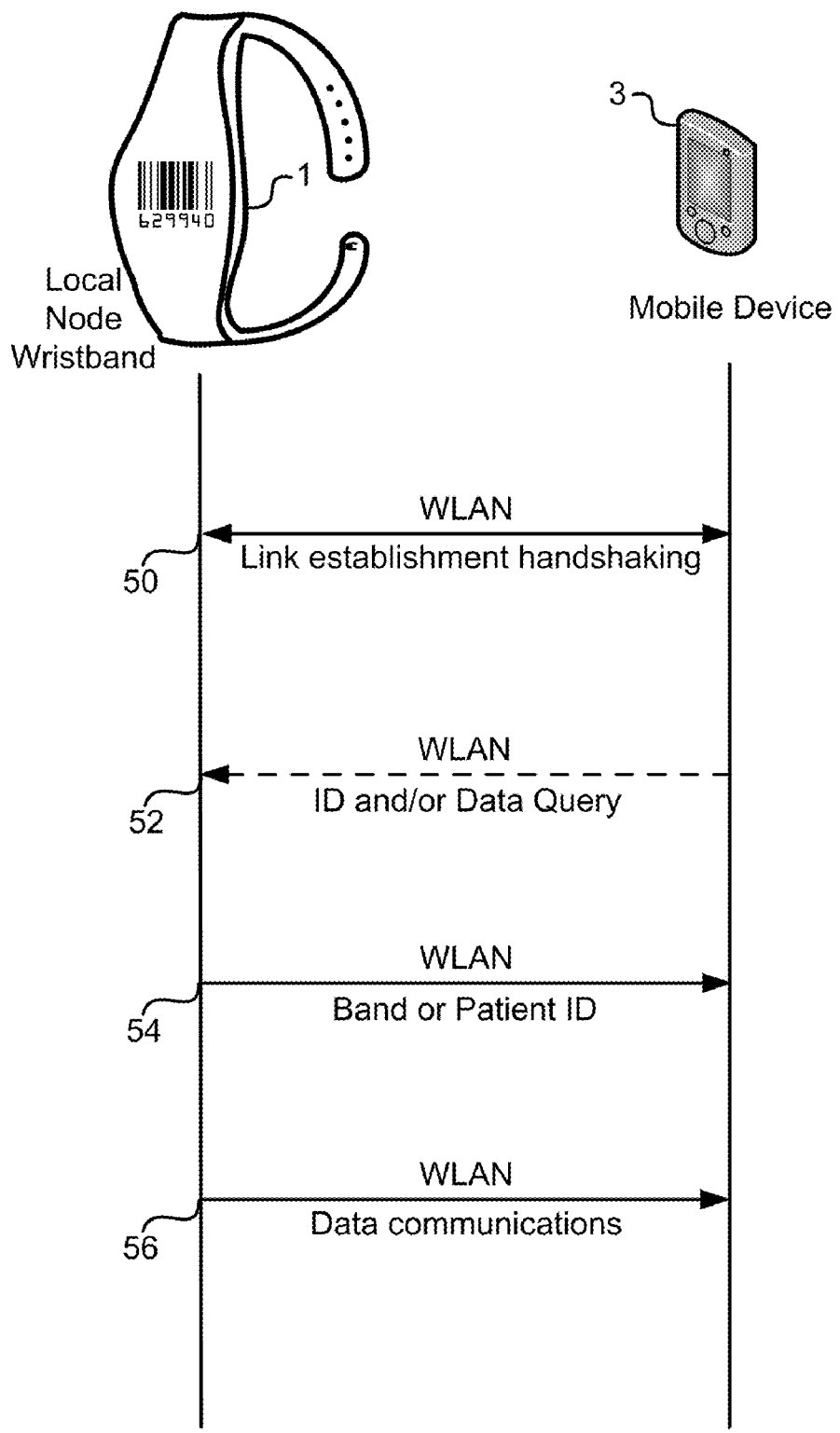
FIG. 3C is a message flow diagram of communications between a gateway wristband and a mobile device according to an embodiment.

In a similar manner, the gateway wristband 1 may establish communications with a mobile computing device 3, such as a PDA. Messages that may be exchanged between the gateway wristband 1 and a mobile computing device 3 are illustrated in FIG. 3C. When the gateway wristband 1 detects signals from a transceiver within the mobile computing device 3, the gateway wristband 1 may began exchanging link establishment handshaking messages 50 with the mobile computing device 3. Once the communication link is established, the mobile computing device 3 may transmit a patient ID or data query request message 52. In response to receiving the patient ID or data query request message 52, the gateway wristband 1 may transmit the patient or wristband ID, message 54, and then transmit sensor data, message 56. The patient ID or data query request message 52 is optional as the gateway wristband 1 may be configured to automatically transmit the patient or wristband ID and sensor data (message 56) to the mobile computing device 3 whenever a communications link is established between the two devices.

Figure 4:
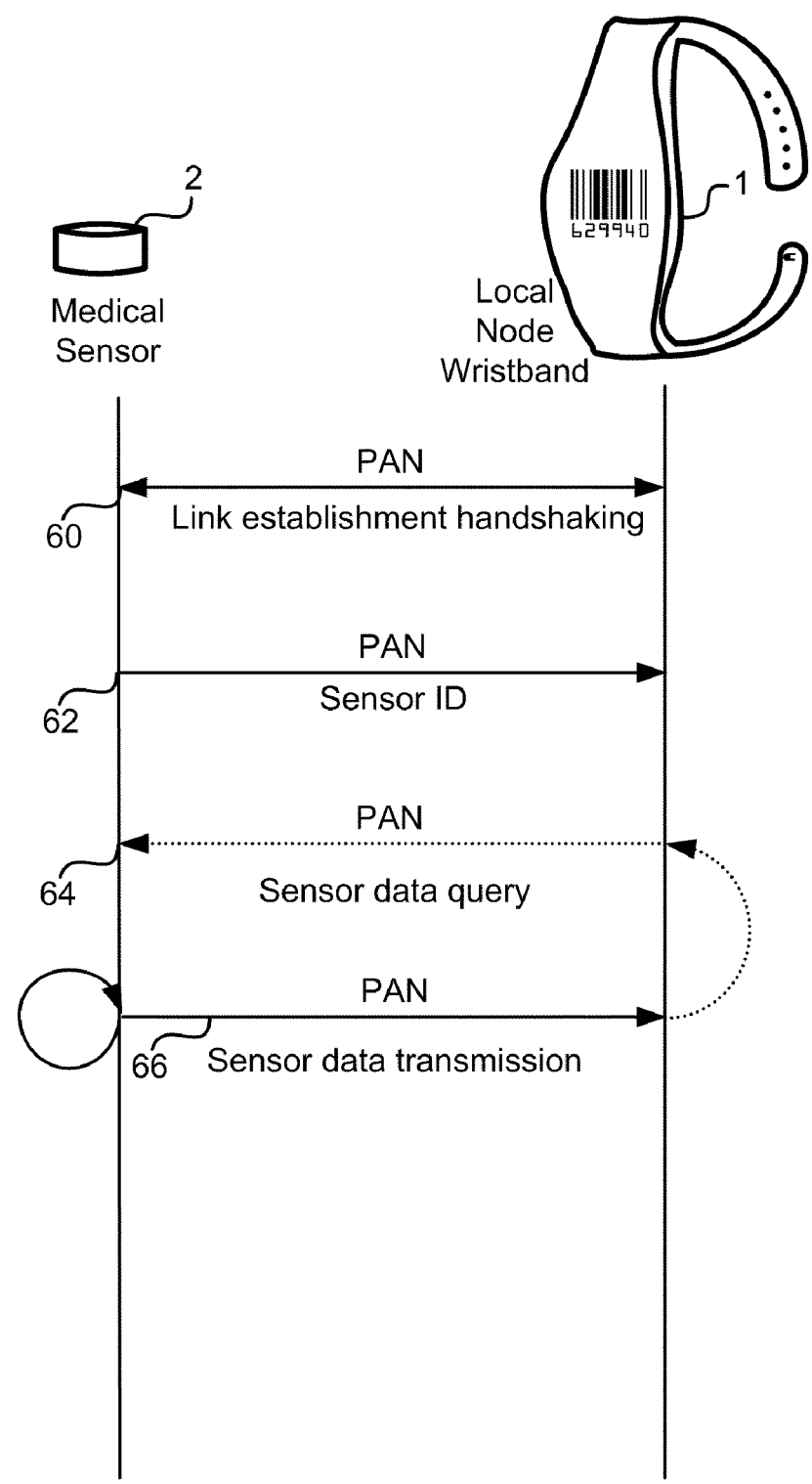
FIG. 4 is a message flow diagram of communications between a gateway wristband and a wireless medical sensor according to an embodiment.

Communications between the gateway wristband 1 and miniaturized electronic medical sensors 2 are illustrated in FIG. 4. When the gateway wristband 1 senses signals from miniaturized electronic medical sensors 2 it may initiate link establishment handshaking messages 60 in order to establish a PAN communication link. These link establishment handshaking messages 60 will be transmitted over the PAN communication link according to the implemented communication protocol. Once a PAN communication link is established, the medical sensors 2 may transmit a sensor ID, message 62, thereby identifying the particular sensor to the gateway wristband 1. Transmitting a sensor ID allows the gateway wristband 1 to receive data from several different sensors, with the data identified or correlated to each sensor ID. This process may continue until communication links are established with all of the miniaturized electronic medical sensors 2 attached on or within the patient. The gateway wristband 1 may query the miniaturized electronic medical sensors 2 by sending a sensor data query message 64 to each sensor. This sensor data query message 64 is optional because the medical sensors may be configured to transmit their data periodically without the need for queries. Periodically or in response to receiving a sensor data query message 64, each miniaturized electronic medical sensor 2 will transmit its sensor data to the gateway wristband 1, message 66. These data transmissions will be repeated for all of the sensors within the PAN network, and may continue over time as the sensors periodically report their data. Optionally, the gateway wristband 1 may periodically start another series of sensor data transmissions (message 66) by transmitting a sensor data query message 64.

Figure 5:
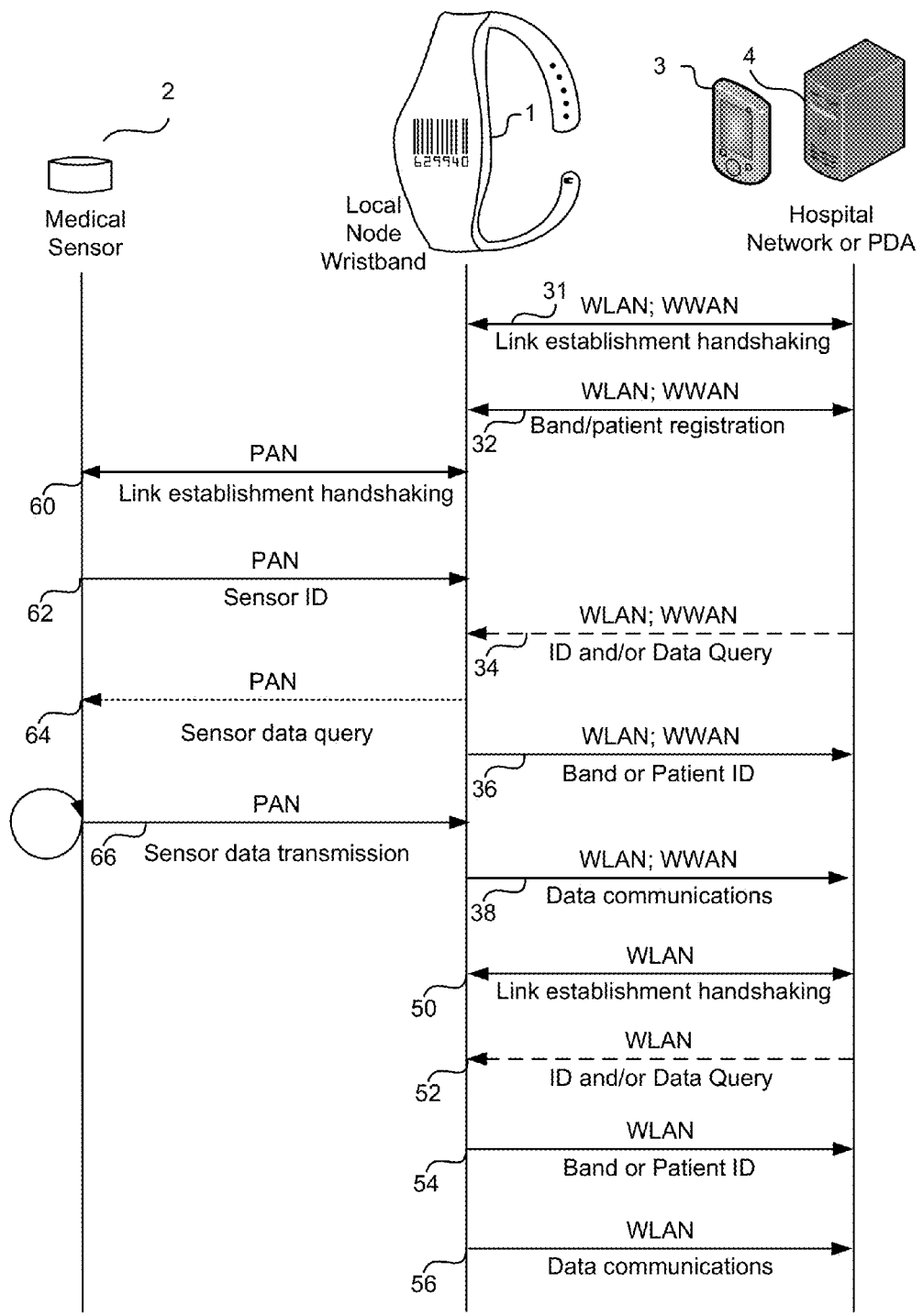
FIG. 5 is a message flow diagram of communications within the system illustrated in FIG. 1.

FIG. 5 illustrates the messages that may be exchanged between miniaturized electronic medical sensors 2, gateway wristbands 1, and hospital networks 4 or mobile computing devices 3. As discussed above, the gateway wristband 1 may register with the hospital network 4 by exchanging link establishment messages (messages 31) and exchanging wristband and patient registration information (registration messages 32). Once registered with the hospital network 4, the gateway wristband 1 may establish communication links with each of the miniaturized electronic medical sensors 2 on a patient by exchanging link establishment handshaking messages 60. The gateway wristband 1 receives the sensor IDs (message 62), and receives the sensor data (message 66) which may be accomplished in response to a sensor data query message 64. If the gateway wristband 1 receives a patient ID or data query message 34 from the hospital network 4 or a mobile computing device 3, it may transmit the wristband or patient ID, message 36. The gateway wristband 1 may also transmit sensor data that it has received, message 38. When the gateway wristband 1 senses a communication link from a mobile computing device 3, it may establish a wireless communication link with that device by exchanging link establishment handshaking messages 50. The mobile computing device 3 may request the patient ID and/or data by transmitting an ID and/or data query request message 52. In response, the gateway wristband 1 may transmit the patient or wristband ID, message 54, and transmit sensor data, message 56.

Figure 6:
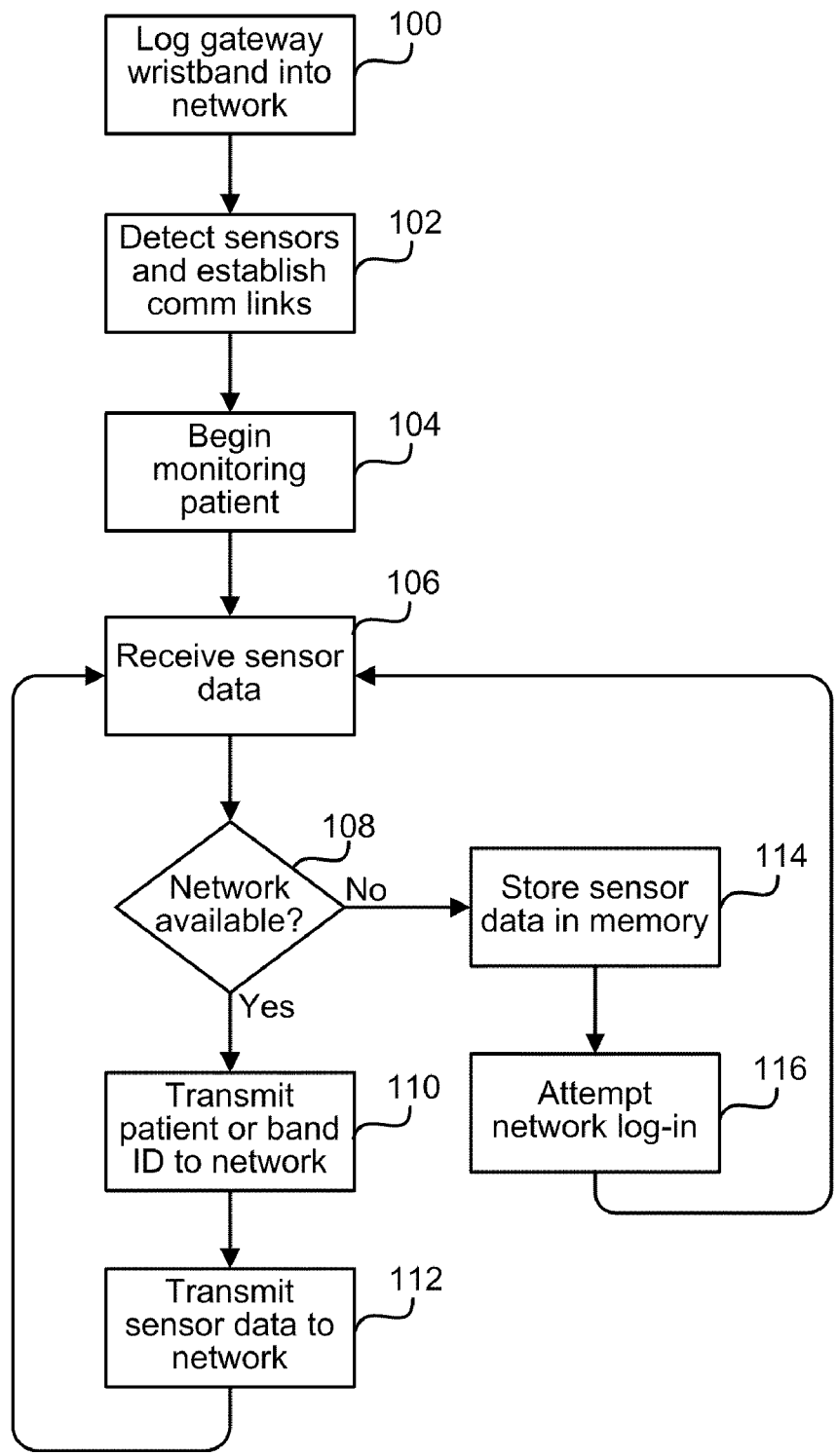
FIG. 6 is a process flow diagram of an embodiment method for relaying patient ID and medical sensor data to a hospital network.

An example of operations that may be implemented with the various embodiments is illustrated in the process flow shown in FIG. 6. As mentioned above, when the gateway wristband 1 senses a wireless network, it may exchange messages sufficient to log the gateway wristband 1 into the network, step 100. The gateway wristband 1 may then detect sensors within range of its personal area network and established communication links with each, step 102. Once all the personal area network communication links are established, the medical sensors and the gateway wristband 1 may begin monitoring the patient, step 104. When the gateway wristband 1 receives sensor data, step 106, it may determine whether the hospital network 4 is available, determination 108. If a communication link is established with the hospital network (i.e., determination 108="Yes"), it may transmit the patient ID to the network, step 110, and transmit the sensor data, step 112. Once all of the data is transmitted, the gateway wristband 1 may return to the processes of receiving sensor data, step 106. However, if there is no communication link with the hospital network 4 (i.e., determination 108="No"), a processor within the gateway wristband 1 may store the sensor data in memory, step 114. The gateway wristband 1 may also periodically attempt to login to the network, step 116. When the sensor data is stored in memory (step 114), the gateway wristband 1 may return to the step of receiving sensor data, step 106.

Figure 7:
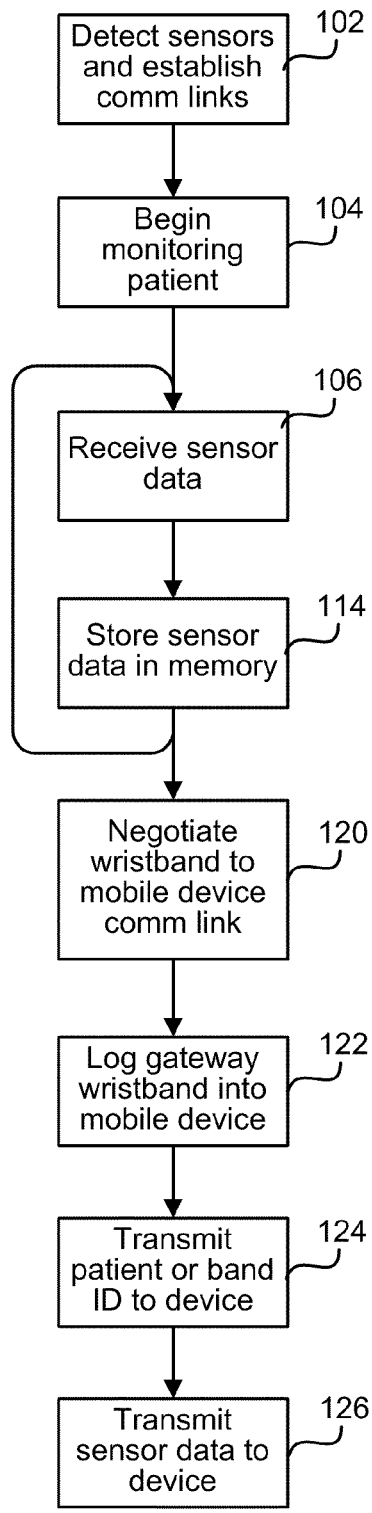
FIG. 7 is a process flow diagram of an embodiment method for relaying patient ID and medical sensor data to a mobile computing device.

Example operations that may be performed by the gateway wristband 1 in communicating with a mobile computing device are illustrated in the process flow diagram shown in FIG. 7. As discussed above, the gateway wristband 1 may detect medical sensors within its personal area network range and establish communications with each, step 102. With those personal area network communication links established the gateway wristband 1 may begin the process of monitoring the patient, step 104, including receiving sensor data, step 106, and storing such a data in memory, step 114. This process may continue until a mobile computing device 3 comes within communication range of the gateway wristband 1. When the gateway wristband 1 senses a network signal from a mobile computing device 3, it may negotiate the wristband-to-mobile computing device communication link, step 120. Once that communication link is established, the gateway wristband 1 may log itself into the mobile computing device, step 122, and transmit the patient or wristband ID, step 124. Once the gateway wristband 1 has identified the patient to the mobile computing device 3, it may begin transmitting the sensor data stored within its memory to the mobile computing device 3, step 126.

Figure 8:
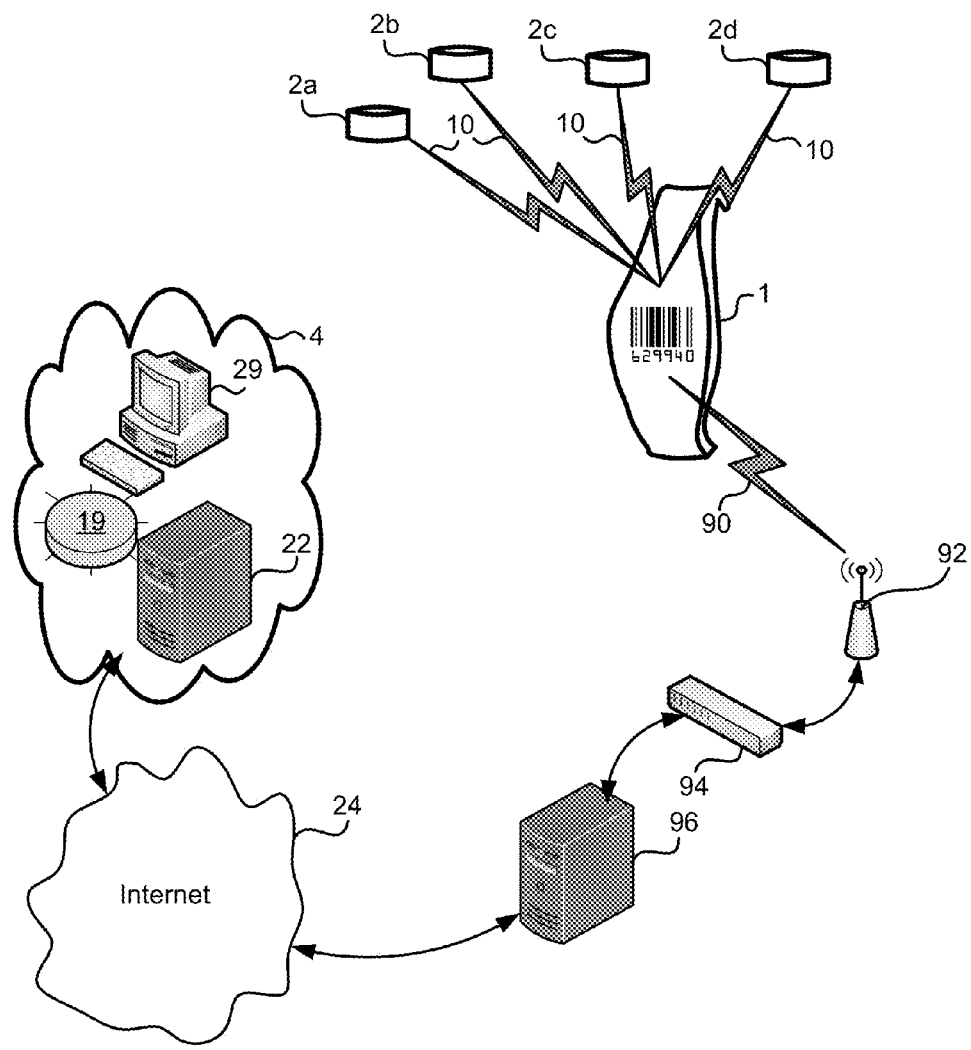
FIG. 8 is a communication system block diagram of a communication network which includes a gateway wristband linking wireless medical sensors on a patient to a hospital communication network via a cellular telephone communication link according to an embodiment.

The gateway wristband 1 may also be configured with a cellular telephone transceiver to enabling connecting the patient and the patient's miniaturized electronic medical sensors to a hospital or other communication network via a cellular data communication network. By way of example, FIG. 8 shows a block diagram of a communication network including a cellular network in which the gateway wristband 1 includes a cellular telephone transceiver for connecting to a cellular network that includes a base station (BS) 92 coupled to a mobile switching center (MSC) 94. In operation, the MSC 94 is capable of routing data calls to and from the gateway wristband 1 via the base station 92 via a cellular wireless communication link 90 when a cellular data call is established. The MSC 94 may be coupled to a server gateway 96 coupled to the Internet 24 so that patient data can be relayed to a hospital network 4 or a medical practitioner's personal computer (not shown). As described above with reference to FIG. 2, the hospital network 4 may include a network router 19 coupled to a server 22 and a plurality of computers or monitors 29.

In the embodiment illustrated in FIG. 8, the gateway wristband 1 is configured to collect and store patient data from miniaturized electronic medical sensors 2a-2d and periodically dial a telephone number to establish a cellular data call (communication link 90) to download the data to a server, such as a server 22 within a hospital network 4. This embodiment may enable patients who must be continuously monitored to return home or move to facilities outside the confines of the hospital network 4. Since the gateway wristband 1 is unobtrusive and configured with software to perform the communications, data storage and data relay functions autonomously, this embodiment should remove many of the burdens associated with remote patient monitoring.

Figure 9:
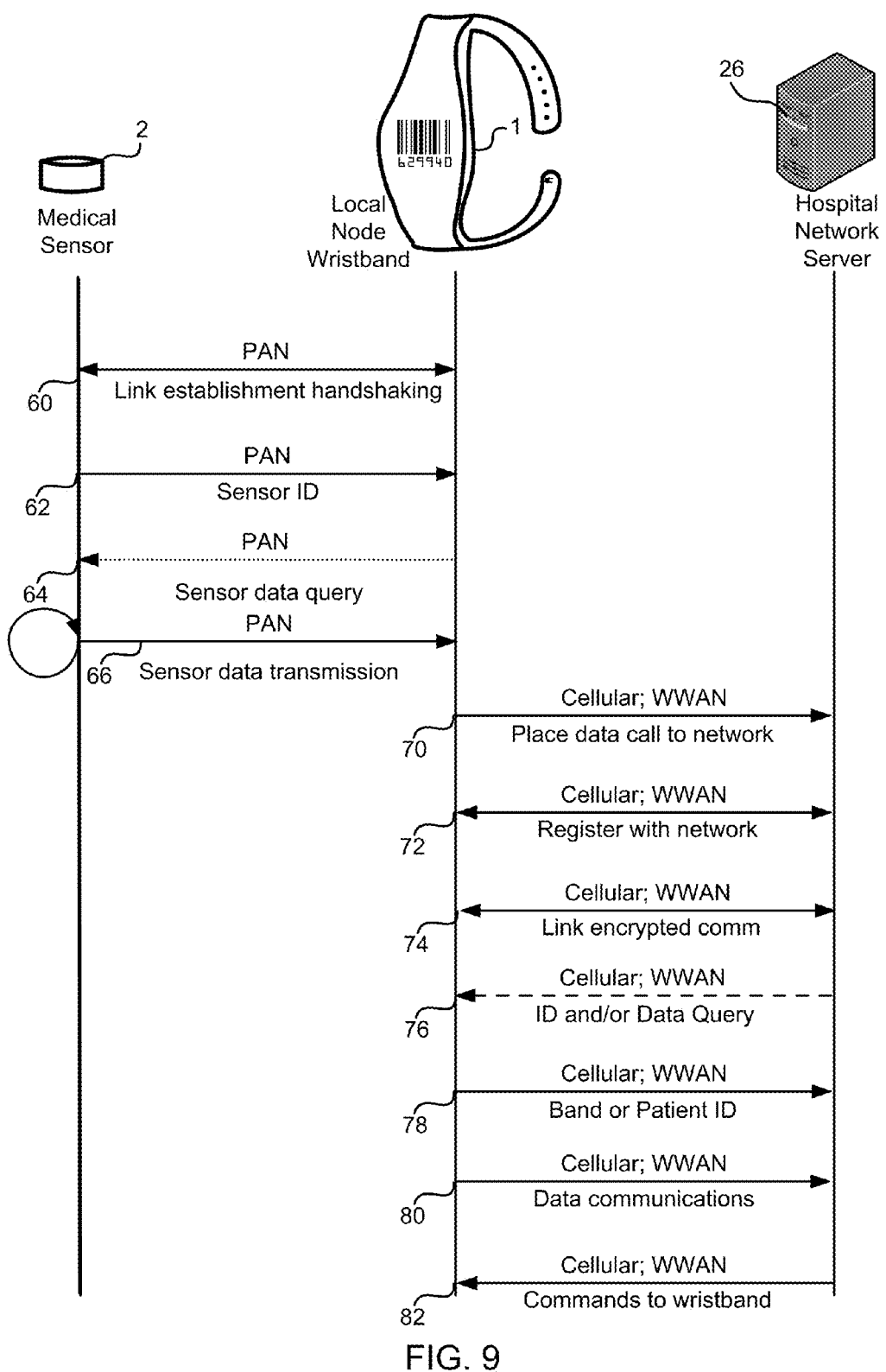
FIG. 9 is a message flow diagram of communications within the system illustrated in FIG. 8.

Messages that may be exchanged in the communication network illustrated in FIG. 8 are illustrated in FIG. 9. As described above, the gateway wristband 1 establishes communication links with each of the miniaturized electronic medical sensors 2 within range of its personal area network, such as by exchanging link establishment handshaking messages 60 and receiving sensor IDs, messages 62. The gateway wristband 1 may periodically query the sensors by sending sensor data query messages 64. In response, the miniaturized electronic medical sensors 2 may transmit their data to the gateway wristband 1 (messages 66) which saves the data in memory. Periodically, such as daily, hourly, or some other frequency, the gateway wristband 1 may place a data call to a cellular network, message 70. The messages and steps required to establish the data call to a network server 22 via a cellular network are consistent with those implemented in standard cellular communication systems. Once a data communication link to a network server 22 is established via the cellular network, the gateway wristband 1 may exchange messages and transmit data necessary to register itself with the server, messages 72. Since patient data is subject to HIPA security requirements, the gateway wristband 1 and the server 22 may negotiate an encrypted communication like by exchanging messages 74. The establishment of such an encrypted data communication link may use protocols that are well-known for such purposes. Once an encrypted communication link is established, the hospital network server 22 may request the patient ID or patient data, optional message 76. This patient ID and/or data query message 76 is optional as the gateway wristband 1 may be configured to automatically transmit such information upon establishing a communication link with the server 22. The gateway wristband 1 may then transmit the patient or wristband ID to the hospital network server, message 78, and communicate the stored sensor data, messages 80. While the data call is established, the hospital network server may also transmit commands to the gateway wristband 1, message 82. Once all of the sensor data has been transmitted and instructions received, the hospital network server 22 or the gateway wristband 1 may terminate the data call.

Figure 10:
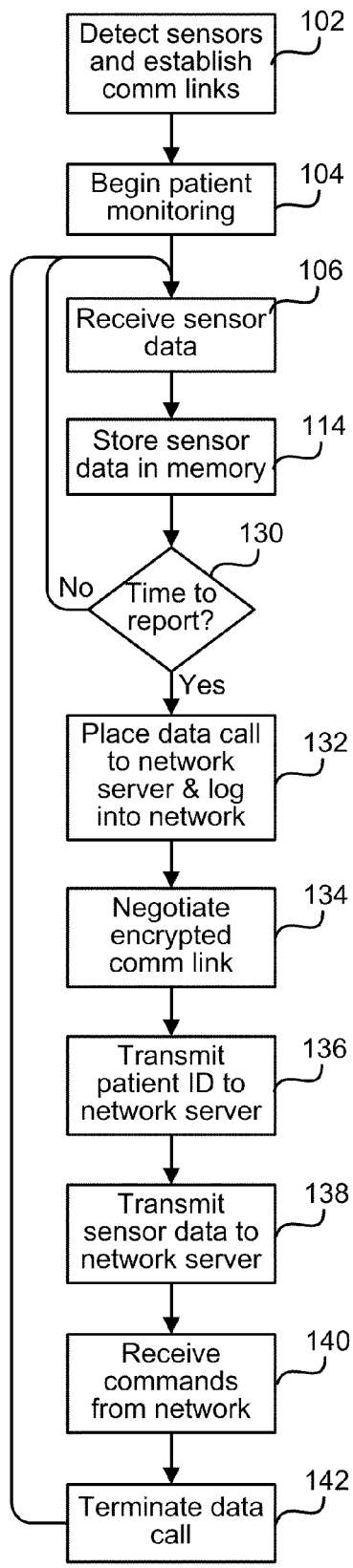
FIG. 10 is a process flow diagram of an embodiment method suitable for use with the communication system illustrated in FIG. 8.

Example operations which may be implemented in the network illustrated in FIG. 8 are illustrated in the process flow diagram shown in FIG. 10. As described above, the gateway wristband 1 establishes communication links with each of the miniaturized electronic medical sensors 2 within range of its personal area network, such as by exchanging link establishment handshaking messages 60 and receiving sensor IDs, messages 62. The gateway wristband 1 may periodically query the sensors by sending sensor data query messages 64. In response, the miniaturized electronic medical sensors 2 may transmit their data in messages 66 which are received by the gateway wristband 1, step 106, and saved in memory, step 114. Periodically, the gateway wristband 1 processor may determine whether it is time to report data to the hospital network, determination 130. If it is not time to report data (i.e., determination 130="No"), the process of receiving sensor data, step 106, and storing the sensor data in memory, step 114, may continue. When it is time to report data (i.e., determination 130="Yes"), the gateway wristband 1 activates its cellular network transceiver to place a data call to the network server 22 of a hospital network 4 (for example) and login to the network, step 132. As part of logging into the hospital network 4, the hospital network server 22 and the gateway wristband 1 may negotiate an encrypted communication link, step 134. With an encrypted communication link established, the gateway wristband 1 may transmit the patient or wristband ID to the network server 22, step 136. The gateway wristband 1 may then transmit the stored sensor data to the server 22, step 138. The network server 22 may also transmit commands to the gateway wristband 1, step 140, such as to change the reporting frequency or initiate/terminate monitoring of particular sensors. Once all data has been transmitted and all commands received and acknowledged the data call is terminated, step 142. At this point the gateway wristband 1 may return to receiving sensor data, step 106.

Figure 11:
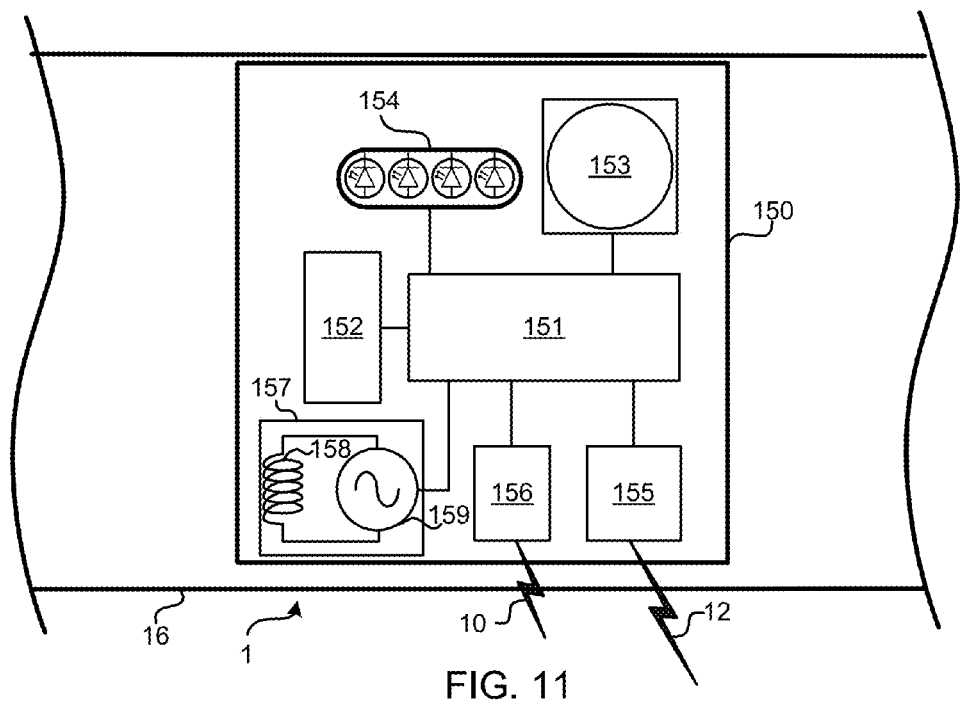
FIG. 11 is a component block diagram of a gateway wristband according to an example embodiment.

Example components that may be included in an exemplary gateway wristband 1 are illustrated in FIG. 11. In an embodiment, the gateway wristband 1 includes a communication interface gateway device 150 that is sealed within a water resistant wristband 16. In a preferred embodiment the water resistant wristband 16 is made of any plastic or rubber substance which is resistant to the sterilizing and cleaning solutions used in a medical facility. The communication interface gateway device 150 may include a processor 151 coupled to memory 152 and a power source, such as a battery 153. In an embodiment, the communication interface gateway device 150 may also include one or more light emitting diodes (LEDs) 154 which may be used to communicate operational status information. A WLAN or WWAN transceiver 155 may be coupled to the processor 151 and configured to establish WLAN or WWAN communication links 12 with a wireless network. A PAN transceiver 156 is also coupled to the processor 151 and configured to establish PAN communication links 10. The communication interface gateway device 150 may also include an induction charging circuit element 157 so that the battery 153 can be recharged by placing the gateway wristband 1 in close proximity to an induction charging system. Such an induction charging circuit element 157 may include an induction coil 158 coupled to a rectifier circuit 159. When an alternating magnetic field is applied to the coil 158, alternating electrical currents are induced in the coil which are rectified by the rectifier circuit 159 to output a charging voltage. The charging voltage may be regulated by the processor 151 and used to charge the battery 153.

In the embodiment described above with reference to FIGS. 8-10, the gateway wristband 1 may include a cellular telephone transceiver as the WWAN transceiver 155. In an embodiment, the WLAN or WWAN transceiver 155 may be configured to communicate with either or both wireless local-area networks (e.g., WiFi) and cellular telephone wireless wide-area networks. In another embodiment, the gateway wristband 1 may include both a WLAN transceiver 155 and a cellular telephone transceiver which is not shown separately but would be represented in a similar manner in a component block diagram.

Figure 12:
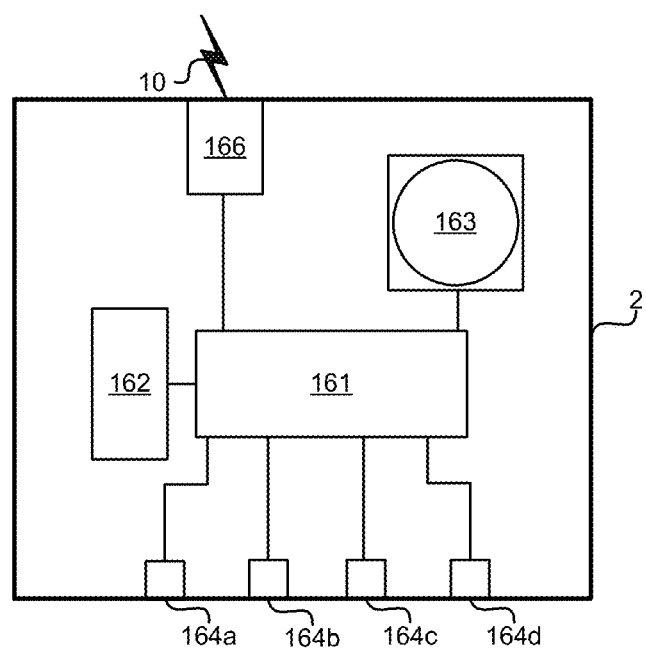
FIG. 12 is a component block diagram of an example wireless medical sensor suitable for use with the gateway wristband illustrated in FIG. 11.

An example miniaturized electronic medical sensor 2 is illustrated in FIG. 12. A miniaturized electronic medical sensor 2 may include a processor 161 coupled to memory 162 and a power supply, such as a battery 163. The miniaturized electronic medical sensor 2 may include a PAN transceiver 166 coupled to the processor 6 and an antenna configured to establish personal area network-range wireless communications, such as using the BlueTooth® protocol. The miniaturized electronic medical sensor 2 may further include one or more medical sensors 164a-164d which may be any of a variety of the medical mechanical, electrical or chemical sensor that are well known in the medical arts.

Figure 13:
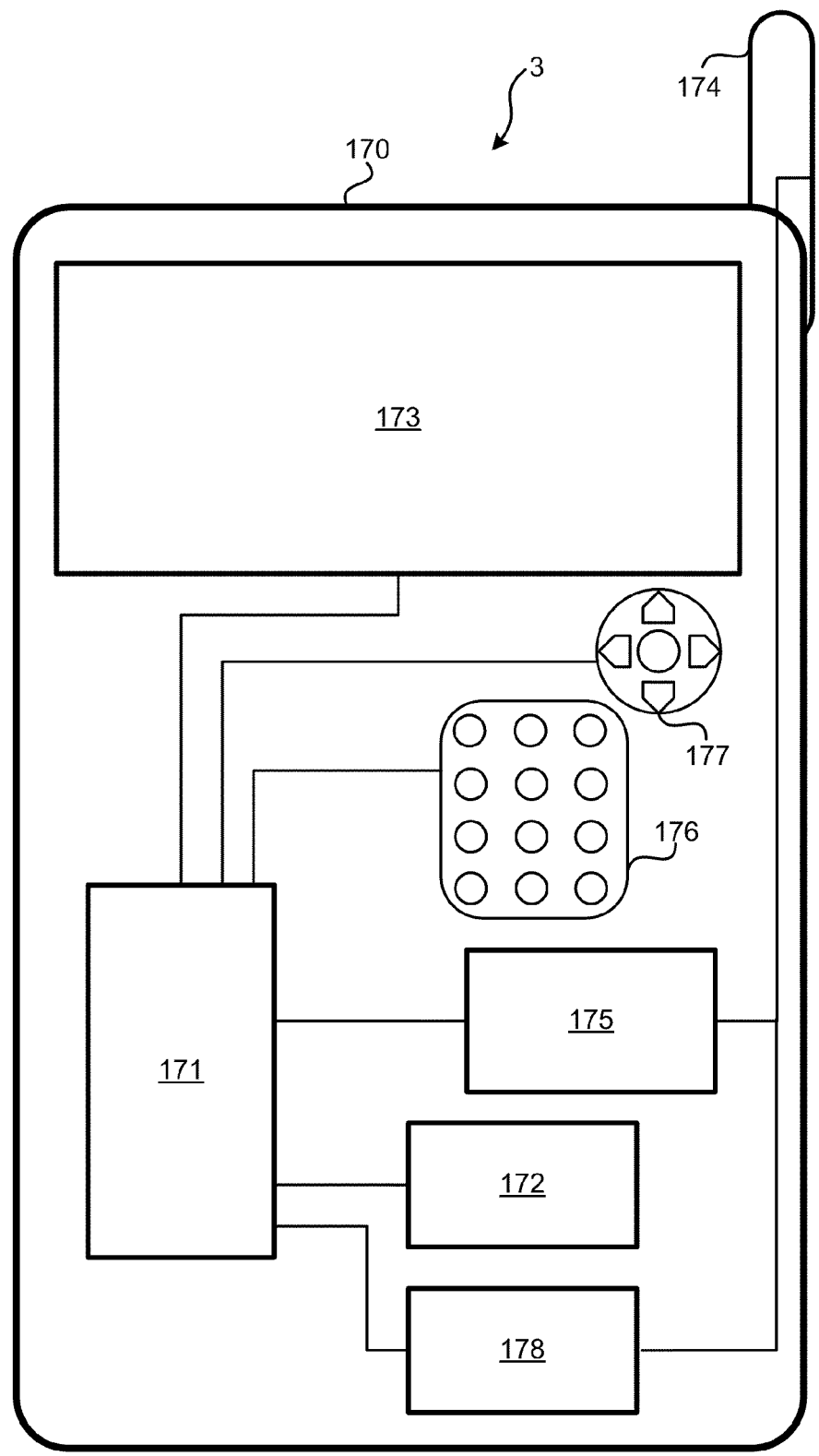
FIG. 13 is a circuit block diagram of an example mobile computing device suitable for use with the gateway wristband illustrated in FIG. 11.

The various embodiments may be used in conjunction with or communicate with a mobile computing device 3, such as a PDA illustrated in FIG. 13. For example, mobile computing devices 3 may include a processor 171 coupled to internal memory 172 and a display 173, such as a liquid crystal display (LCD), all included within a case or housing 170. Additionally, the mobile computing device 3 may have an antenna 174 for sending and receiving electromagnetic radiation that is connected to a wireless data link transceiver 175 coupled to the processor 171. Such a WLAN wireless data link transceiver 175 may be configured according to any known wireless wide-area communication protocol, such as IEEE802.11 or WiMax, in order to connect with a hospital network 4. Mobile computing devices 3 may also include a second wireless transceiver, such as a PAN transceiver 178 coupled to the processor 171 and the antenna 174 to enable it to communicate with the gateway wristband 1 or with a patient's miniaturized electronic medical sensors 2. Mobile computing devices 3 also typically include a key pad 176 or miniature keyboard and menu selection buttons or rocker switches 177 which may serve as pointing devices for receiving user inputs for positioning a cursor within the display 173.

In the various devices, the processors 151, 161 and 171 may be any programmable microprocessor, microcomputer or multiple processor chip or chips that can be configured by software instructions to perform a variety of operations, including the operations of the various embodiments described above. In some devices, multiple processors 151, 161 and 171 may be provided, such as one processor dedicated to wireless communication functions and one processor dedicated to running other applications. Typically, software instructions may be stored in the internal memory 152, 162, 172 before they are accessed and loaded into the processor 151, 161, 171. In some devices, the processor 151, 161, 171 may include internal memory sufficient to store the software instructions. For the purposes of this description, the term memory refers to all memory accessible by the processor 171151, 161, 171, including connected memory units 152, 162, 172 and memory within the processor 151, 161, 171 itself. Sensor data will typically be stored in the memory unit 152, 162, 172. In many devices, the memory 152, 162, 172 may be a volatile or nonvolatile memory, such as flash memory, or a mixture of both.

Those of skill in the art would appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Skilled artisans may implement the described functionality in varying ways for each particular application, but such implementation decisions should not be interpreted as causing a departure from the scope of the present invention.

In various embodiments the functions described above may be implemented in hardware, software, firmware, or any combination thereof. Whether such functionality is implemented as hardware or software depends upon the particular application and design constraints imposed on the overall system. If implemented in software, the functions may be stored as one or more instructions or codes on a computer-readable medium, i.e., non-transitory computer-readable medium. Computer-readable media includes computer storage media that facilitates transfer of a computer program from one place to another. A storage medium may be any available media that can be accessed by a computer. By way of example, and not limitation, such non-transitory computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of non-transitory computer-readable media.

The order in which the steps of a method described above and shown in the figures is for example purposes only as the order of some blocks may be changed from that described herein without departing from the spirit and scope of the present invention and the claims.

The steps of a method or algorithm described in connection with the aspects disclosed herein may be embodied directly in hardware, in a software module executed by a processor, or in a combination of the two. A software module may reside in processor readable memory which may be any of RAM memory, flash memory, ROM memory, EPROM memory, EEPROM memory, registers, hard disk, a removable disk, a CD-ROM, or any other form of storage medium known in the art. An exemplary storage medium is coupled to a processor such that the processor can read information from, and write information to, the storage medium. In the alternative, the storage medium may be integral to the processor. The processor and the storage medium may reside in an ASIC. The ASIC may reside in a user terminal or mobile device. In the alternative, the processor and the storage medium may reside as discrete components in a user terminal or mobile device. Additionally, in some aspects, the blocks and/or actions of a method or algorithm may reside as one or any combination or set of codes and/or instructions on a machine readable medium and/or computer readable medium, which may be incorporated into a computer program product.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A communication gateway wristband, comprising:
a wristband;
a processor sealed within the wristband;
a first wireless transceiver coupled to the processor, the first wireless transceiver configured to communicate according to a first protocol;
a second wireless transceiver coupled to the processor, the second wireless transceiver configured to communicate according to a second protocol; and
a memory coupled to the processor,
wherein the processor is configured with software instructions to perform steps comprising:
  receiving a patient identifier from an external network;
  receiving data from at least one medical sensor via the first wireless transceiver;
  communicating the received patient identifier to the external network via the second wireless transceiver; and
  relaying the received data to the external network via the second wireless transceiver.

2. The communication gateway wristband of claim 1, wherein the processor is configured with software instructions to perform steps further comprising:
sensing the at least one medical sensor;
establishing a communication link between the at least one medical sensor and the first wireless transceiver; and
receiving a sensor identifier via the first wireless transceiver.

3. The communication gateway wristband of claim 1, wherein the processor is configured with software instructions to perform steps further comprising:
sensing the external network; and
establishing a communication link between the external network and the second wireless transceiver.

4. The communication gateway wristband of claim 1, wherein the processor is configured with software instructions to perform steps further comprising:
storing the received data in the memory.

5. The communication gateway wristband of claim 3, wherein the processor is configured with software instructions to perform steps further comprising:
establishing an encrypted communication link between the second wireless transceiver and the external network,
wherein the patient identifier and the received data are transmitted via the encrypted communication link.

6. The communication gateway wristband of claim 1, wherein the patient identifier stored in the memory comprises an identifier assigned to the patient.

7. The communication gateway wristband of claim 1, wherein the patient identifier comprises an identifier of the communication gateway wristband that is correlated to the patient in a data table stored in the external network.

8. The communication gateway wristband of claim 1, further comprising:
a battery coupled to the processor; and
an induction charging circuit coupled to the processor.

9. The communication gateway wristband of claim 1, wherein:
the processor, first and second transceivers and memory are sealed within the wristband in a waterproof manner; and
the wristband is configured to be resistant to sterilization and cleaning solutions used in hospital facilities.

10. The communication gateway wristband of claim 1, wherein the processor is configured with software instructions to perform steps further comprising:
sensing an external wireless communication device;
establishing a communication link between the second transceiver and the external wireless communication device according to the second communication protocol;
communicating the patient identifier to the external wireless communication device via the second transceiver; and
relaying the received data to the external wireless communication device via the second transceiver.

11. A communication system, comprising:
a first wireless network configured to communicate via a first wireless communication protocol;
at least one miniaturized electronic medical sensor configured to communicate via a second wireless communication protocol; and
a communication gateway wristband, the communication gateway wristband comprising:
  a wristband;
  a processor sealed within the wristband;
  a first wireless transceiver coupled to the processor, the first wireless transceiver configured to communicate according to the first communication protocol;
  a second wireless transceiver coupled to the processor, the second wireless transceiver configured to communicate according to the second communication protocol; and
  a memory coupled to the processor,
  wherein the processor is configured with software instructions to perform operations comprising:
    receiving a patient identifier from the first network;
    receiving data from the at least one miniaturized electronic medical sensor via the first wireless transceiver;
    communicating the received patient identifier to the first network via the second wireless transceiver; and
    relaying the received data to the second wireless network via the second wireless transceiver.

12. The communication system of claim 11, further comprising:
an external wireless communication device,
wherein the processor is configured with software instructions to perform operations further comprising:
  sensing the external wireless communication device;
  establishing a communication link between the second transceiver and the external wireless communication device according to the second communication protocol;
  communicating the patient identifier to the external wireless communication device via the second transceiver; and
  relaying the received data to the external wireless communication device via the second transceiver.

* * * * *